United States Patent
Takenaga et al.

[11] Patent Number: 5,723,121
[45] Date of Patent: Mar. 3, 1998

[54] SUGAR MODIFIED INTERFERON

[76] Inventors: Mitsuko Takenaga, 30-1, Sugao 2-chome, Miyamae-ku, Kawasaki-shi, Kanagawa 216; Katsukiyo Sakurai, 527-6, Zohshiki 2-chome, Higashiyamato-shi, Tokyo 207; Rie Igarashi, 8-2, Minami-ikuta 5-chome, Tama-ku, Kawasaki-shi, Kanagawa 214; Yutaka Mizushima, 1-11, Umegaoka 1-chome, Setagaya-ku, Tokyo 154, all of Japan

[21] Appl. No.: 812,920

[22] Filed: Mar. 10, 1997

Related U.S. Application Data

[63] Continuation of Ser. No. 288,746, Aug. 16, 1994, abandoned.

[30] Foreign Application Priority Data

Aug. 23, 1993 [JP] Japan .................. 5-227816

[51] Int. Cl.$^6$ .................. A61K 38/21; G07K 17/10
[52] U.S. Cl. .................. 424/85.4; 514/2; 514/12; 514/21; 530/351; 530/402
[58] Field of Search .................. 424/85.4, 85.5, 424/85.6, 85.7; 514/2, 12, 21; 530/351, 402

[56] References Cited

U.S. PATENT DOCUMENTS

| | | | |
|---|---|---|---|
| 4,377,567 | 3/1983 | Geho | 424/1 |
| 5,037,969 | 8/1991 | Minami et al. | 536/4.1 |

FOREIGN PATENT DOCUMENTS

| | | | |
|---|---|---|---|
| 0009842 | 9/1979 | European Pat. Off. | A61K 9/50 |
| 0589378 | 9/1993 | European Pat. Off. | C07K 15/14 |
| 1102099 | 4/1989 | Japan | C07K 15/14 |
| WO9222310 | 6/1992 | WIPO | A61K 37/02 |

OTHER PUBLICATIONS

Chemical Abstract: 121; 177704a, 1989.
Chemical Abstract: 111; 201591c, 1994.
J. Biol. Chem., 251, 1296–1302 (1976).
J. Biol. Chem., 258, 199–202 (1983).

*Primary Examiner*—Ponnathapura Achutamurthy

[57] ABSTRACT

Sugar-modified interferon, modified with at least one galactose residue, which is a binding reaction product between lactose lactone and interferon is disclosed. The sugar-modified interferon, which can be obtained through simple chemical manipulation on IFN, has improved accumulating properties in the liver and enhanced physiological activities as compared with unmodified IFN.

15 Claims, 1 Drawing Sheet

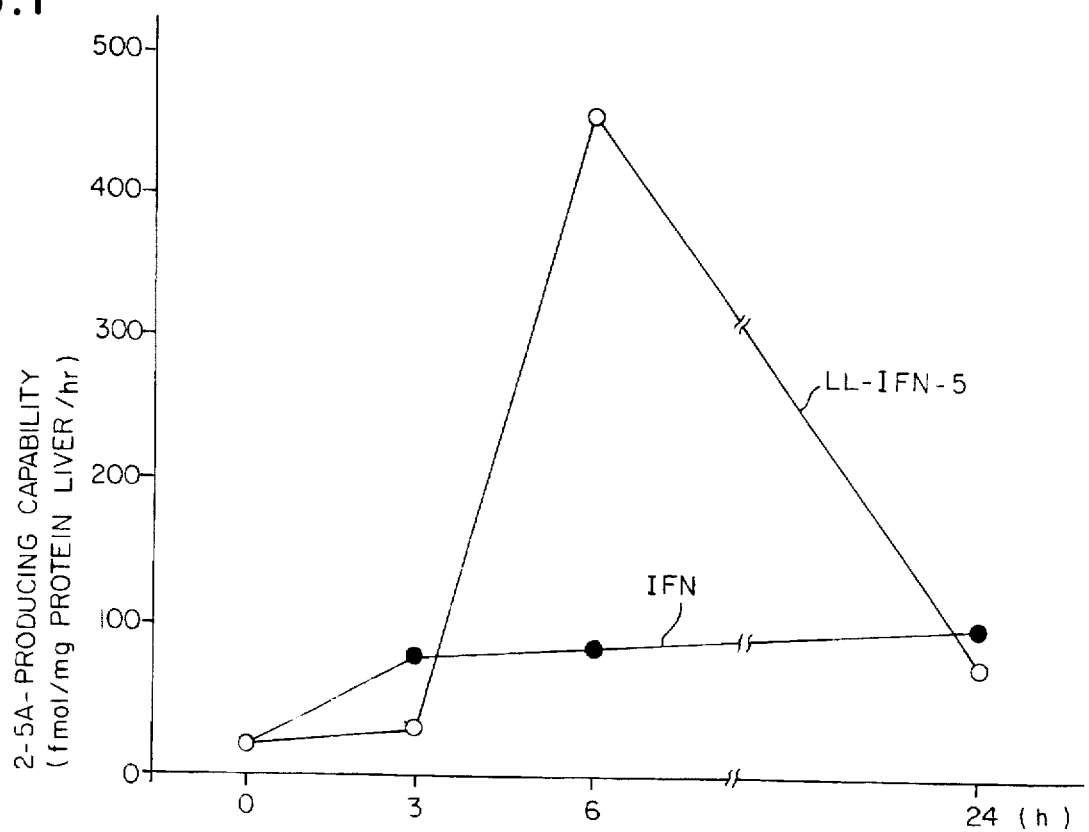

SUGAR MODIFIED INTERFERON

This is a continuation of U.S. Ser. No. 08/288,746 filed 16 Aug. 1994, now abandoned.

FIELD OF THE INVENTION

This invention relates to synthetic sugar-modified interferon.

BACKGROUND OF THE INVENTION

In recent years, many attempts have been made to utilize physiologically active proteins or glycoproteins isolated from living bodies as medicines or diagnostic agents. To make effective and specific use of these biological substances, it is considered essential to improve their in vivo stability and to let them manifest (or enhance) their signal activities in metabolism or at intracellular sites or for recognition of receptors or target cells. In this connection, chemical modification of proteins seems to be a promising approach for improvement in stability in blood, enhancement of the signal activities to promote incorporation into target cells or target organs, enhancement of the physiological activities, and possibly production of an additional new physiological activity.

Affinity between galactose and the liver was reported in relation to accumulation in the liver as a target organ (Kawasaki T. & Ashwell. G., *J. Biol. Chem.*, Vol. 251, p. 1296 (1976) and Lee Y. C. et al., *J. Biol. Chem.*, Vol. 258, p. 199 (1983)). The finding disclosed in the report provides for binding galactose-terminated sugar to a protein having an effective physiological activity on hepatic diseases, such as liver cancer (hepatic carcinoma), liver cirrhosis and hepatitis, thereby increasing the intake of the protein into the liver and heightening the therapeutic efficacy.

For example, known sugar-modified proteins include physiologically active proteins modified with β-D-galactopyranosyl polyethyleneglycol (see U.S. Pat. No. 5,037,969 corresponding to JP-A-63-152393, the term "JP-A" as used herein means an "unexamined published Japanese patent application"). It is known that a galactose is introduced into physiologically active proteins with sugar derivative, which has a galactose residue and a reactive functional group, such as 1-deoxy-1-β-cyanomethylthio-D-galactopyranose (EP-A-0 589 378 and JP-A-4-20285). It is also known that interferon is encapsulated in or associated with lipid membrane structures in the form of vesicles or liposomes which comprise a mixture of a major portion of a polar lipid and a minor portion of a digalactosyl drivative having at least one fatty substituent (U.S. Pat. No. 4,377,567). A conjugated medicine of interferon with asialoglycoprotein containing a galactose is disclosed in (WO92/22310). A technique for preparing glycoproteins containing a large amount of galactose.galactose-terminated sugar chains through gene manipulation is also known (see JP-A-1-102099).

However, these conventional techniques for chemical or biochemical modification are disadvantageous in that complicated steps are involved; some reaction conditions adopted induce denaturation of a physiologically active protein; necessary regents as raw materials are expensive or difficult to obtain; or special eukaryocytes need to be used for gene expression as a glycoprotein. None of the conventional techniques have achieved satisfactory results and been put to practical use.

SUMMARY OF THE INVENTION

An object of the present invention is to provide sugar-modified interferon (hereinafter abbreviated as INF) having improved accumulating properties in the liver and enhanced physiological activities, which can be obtained through simple chemical manipulation under a mild reaction condition on INF.

As a result of extensive investigations with the above object, the present inventors have obtained sugar-modified IFN, specifically IFN having galactose introduced thereinto, and found that this sugar-modified IFN shows high retention of IFN activities in spite of the sugar modification and exhibits extremely high accumulating properties in the liver.

The present invention provides sugar-modified IFN, modified with a galactose residue, which is a binding reaction product between lactose lactone and IFN.

Preferred mode of sugar-modified IFN of the present invention is sugar-modified IFN produced by binding a carbonyl group of lactose lactone represented by formula (a) with an ε-amino group of a lysine residue and/or an amino group at the N-terminal of IFN.

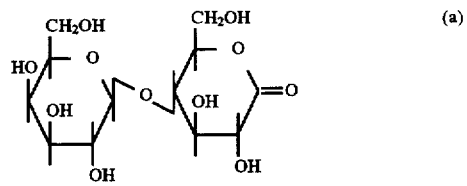

The present invention further provides a process for producing sugar-modified IFN which comprises reacting lactose lactone with IFN in an aqueous solvent at a temperature of from 0° to 45° C.

The process for producing sugar-modified IFN of the present invention is preferably performed in the presence of a surfactant which does not contain an amino group reactive with lactose lactone. Preferred examples of such surfactant are an anionic surfactant and a nonionic surfactant. Alkylsulfates such as dodecyl sulfate are more preferable.

The present invention furthermore provides sugar-modified IFN composition, such as an injectable solution, which comprises the above-mentioned sugar-modified IFN and conventional carriers, diluents, stabilizing agents and/or excipients.

BRIEF DESCRIPTION OF THE DRAWING

FIG. 1 is a graph showing 2–5A-producing capability of sugar-modified IFN (LL-IFN-5) and untreated IFN-α (IFN) in the liver of ICR mice with time.

DETAILED DESCRIPTION OF THE INVENTION

Lactose lactone (CAS Registry No. 5965-65-1) is a known substance disclosed in U.S. Pat. No. 5,310,542 corresponding to EP-A-551675, EP-A-550281, U.S. Pat. No. 5,296,588 corresponding to EP-A-550106 and EP-A-506952. Lactobionic acid 1,5-lactone, Lactobiono-1,5-lactone, Lactobionolactone and Lactonolactone are used as synonymous with "lactose lactone". Lactose lactone can be prepared as follows.

Lactose is oxidized in a lower alcohol (e.g., methanol) with an oxidizing agent, such as iodine, to ring open the reducing terminal glucopyranose to obtain lactobionate (CAS Registry No. 96-82-2), which is then treated under acidic conditions using, for example, a strongly acidic cation exchange resin (e.g., Dowex 50 (H$^+$)) for dehydrating cyclization to obtain lactose lactone (lactobiono-1,5-lactone) (see Yuichi Ohya, Toshiaki Takei, Haruya Fukushima and Tatsuro Ouchi, *J. Macromol. Sci., Chem.*, A28(8), 743–760 (1991), Kazukiyo Kobayashi, Hiroshi Sumitomo and Yoshimitsu Ina, *Polym. J.* (Tokyo), 17(4), 567–575 (1985) and Williams Taffy J., Nike R. Plessas and Irwin J. Goldstein, *Carbohydr. Res.*, 67(1), C1–C3 (1978)).

IFN which is to be reacted with lactose lactone is Dot limited in its type,.origin, amino acid sequence or sugar chain structure as long as it has at least one primary amino group as a functional group capable of binding to lactose lactone. The IFN may be a polypeptide consisting of amino groups, or an IFN derivative having a sugar chain and/or other modifying groups. For example, IFN species which can be used in the present invention include those of animal origin inclusive of human, monkey, dog, swine, rabbit, mouse or rat (inclusive of those obtained by tissue culture), those obtained by gene engineering, and synthetic ones.

Preferred types of IFN are an IFN-α called alpha-interferon, LeIF, leukocyte interferon or lymphoblastoid interferon, and an IFN-β called beta-interferon, fibroblast interferon or FIF.

IFN-α is produced by peripheral blood leukocytes or lymphoblastoid cells upon exposure to live or inactivated virus, double-stranded RNA, or bacterial products.

General information concerning IFN-α is referred to the following publications.

I. Gresser, "Production by virus stimulated human leukocyetes", Proc. Soc. Exp. Biol. Med. 108, 799 (1961); C. B. Anfinsen et al., "Purification", Proc. Nat. Acad. Sci. USA, 71, 3139 (1974); K. Berg et al., J. Immunol., 114, 640 (1975); W. P. Levy et al., "Partial sequence of human leukocyte IFN", Proc. Nat. Acad. Sci. USA, 77, 5102 (1980); K. C. Zoon et al., "Partial sequence of human lymphoblastoid IFN", Science, 207, 527 (1980); S. Nagata et al., "Production by recombinant DNA technology", Nature, 284, 316 (1980); D. V. Goeddel et al., ibid. 287, 411 (1980); "Series of articles on therapeutic use", Eur. J. Hematol., 45, Supple., 1–39 (1990); and M. Ho, "Review of clinical efficacy in viral infections", Ann. Rev. Med., 38, 51–59 (1987).

IFN-α obtained by gene engineering technology is exemplified by rIFN-αA, B, C, D, E, F, G, H, I and J (EP 43980 B and EP 211148 B).

Specific examples of IFN-α derivative include Interferon α-2a, Interferon α-2b, Interferon α-2c, Interferon α-n1 and Interferon α-n3.

IFN-α marketed as a medicine and IFN-α which is on sale as a reagent for research can be used in the present invention. Such commercially available IFN-α is exemplified as follows.

Alferon (Interferon Sciences), Berofor Alpha 2 (Boehringer, Ing.), Canferon (Takeda), Cibian (Yamanouchi), Intron A (Schering), Intron a (Schering), Roferon-A (Roche), Sumiferon (Sumitomo), Wellferon (Burroughs Wellcome), human leukocyte interferon (Sigma Chemicals, Catalog No. I1008) and human lymphoblastoid interferon (Sigma Chemicals, Catalog Nos. I9887 and I5511).

IFN-β is cytokine with antiviral, antiproliferative and immunomodulatory activity and produced by fibroblasts in response to stimulation by live or inactivated virus or by certain synthetic polynucleotides. One of the type I interferons is a glycoprotein containing 166 amino acids; mol wt approx 20,000 daltons.

General information concerning IFN-β is referred to the following publications.

E. A. Hayell and J. Vilcek, "High yield production by human fibroblast cell cultures", Antimicrob. Ag. Chemother. 2, 476 (1972); C. B. Anfinsen et al., "Partial purification", Proc. Nat. Acad. Sci. USA, 71, 3139 (1974); K. Berg et al., J. Immunol., 114, 640 (1975); E. Knight, Jr., "Purification and initial characterization", Proc. Nat. Acad. Sci. USA, 73, 520 (1976); R. L. Cavalieri et al., "Comparison with interferon-α, q.v.", ibid, 74, 3287 (1977); W. A. Carter and J. S. Horoszewicz, "Review of production, purification and potential applications", Pharmacol. Ther., 8, 359–377 (1980); E. Knight, Jr. et al., "Amino acid analysis, partial sequence", Science, 207, 525 (1980); S. Stein et al., Proc. Nat. Acad. Sci. USA, 77, 5716 (1980); T. Taniguchi et al., "Amino acid sequence", Gene, 10, 11 (1980); T. Taniguchi et al., "Production by recombinant DNA technology", Proc. Nat. Acad. Sci. USA, 77, 5230 (1980); R. Defyrick et al., Nature, 285, 542 (1980); D. V. Goeddel et al., Nucleic Acids Res., 8, 4057 (1980); E. C. Borden et al., "Comparative antiproliferative activity of natural IFNs-α and β", Cancer Res., 42, 4948 (1982); P. K. Lillis et al., "Clinical evaluation of recombinant HuIFN-β in colorectal cancer", Cancer Treat. Rep., 71, 965 (1987); P. L. Triozzi et al., ibid., 983; and M. Glezerman et al., "Clinical evaluation of natural form in herpes simplex infections", Lancet 1, 150 (1988).

Specific examples of IFN-β derivative include Betaseron (Synthetic mutein having a serine substituted for the cysteine residue at position 17 of the native molecule. Preparation: D. F. Mark et al., Proc. Nat. Acad. Sci. USA, 81, 5662 (1984)).

IFN-β marketed as a medicine and IFN-β which is on sale as a reagent for research can be used in the present invention. Such commercially available IFN-β is exemplified as follows.

Betaseton (Triton Biosci.), Feron (Toray), Fiblaferon (Rentschler), Frone (Serone) and Naferon (Sclavo).

The functional group of IFN capable of binding to lactose lactone is not particularly limited as long as it is reactive with the carboxyl group (carbonyl group) of a galactose derivative resulting from ring opening of lactose lactone. Preferably used are primary amino group which is usually ε-amino group of lysine residues or N-terminal free amino group of polypeptide chain.

Reaction between lactose lactone and the functional group of IFN efficiently gives sugar-modified IFN having a galactose residue in the intramolecular and/or terminal functional group(s) of IFN molecule.

The rate of sugar modification in the sugar-modified IFN, that is, the rate of binding of a galactose residue is subject to variation depending on the reaction conditions, such as the amount of lactose lactone used and the reaction time. What is required is that the modified IFN contains at least one sugar residue per IFN molecule. Preferably about 10 to 80%, more preferably about 30 to 60% of primary amino groups of IFN are modified with galactose residue. That is, in the case wherein IFN molecule has about ten primary amino groups, IFN contains preferably 1 to 8, more preferably 3 to 6 galactose residues. The rate of sugar modification can be selected arbitrarily according to the end use of the sugar-modified IFN.

The primary amino group as a functional group of IFN includes an ε-amino group of a lysine residue and an amino group at the N-terminal of polypeptide chain. Formation of sugar-modified IFN can be represented by the following reaction formula, taking for instance reaction between lactose lactone and IFN only through acid amido bond between the above-mentioned primary amino group of IFN and carbonyl group of lactose lactone:

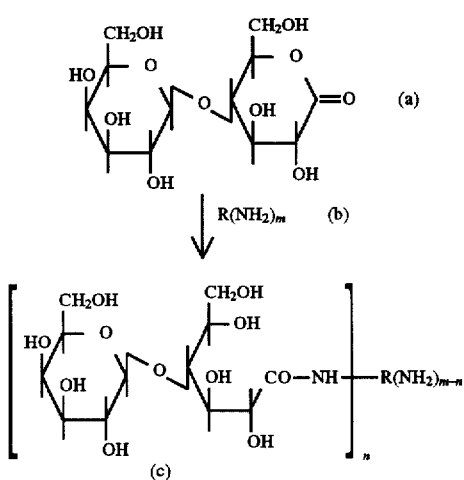

wherein (a) is the structural formula of lactose lactone; (b) represents IFN; (c) is the resulting sugar-modified IFN; m represents the number of primary amino groups in IFN; n represents the number of acid amido bonds; R represents the IFN skeleton; and m is not smaller than n, preferably larger than n.

In the case of IFN wherein m is about 10 (10 lysine residues, Occasionally containing an amino group at the N-terminal), n is from 1 to 8, preferably from 3 to 6.

The reaction is preferably carried out in an aqueous solvent, such as water or a buffer solution (e.g., a borate buffer, a phosphate buffer, or a phosphate-buffered saline solution (PBS)) at such a temperature that does not denature or deactivate IFN, usually from 0° C. to 45° C., and preferably from 4° C. to 30° C., more preferably around room temperature, in a broad pH range of from about 3 to 10, preferably around neutrality, for a period of from about 0.5 to 100 hours, and preferably from 20 to 50 hours. The amounts of lactose lactone and IFN to be used are decided through preliminary experimentation, taking the physiological activities of the resulting sugar-modified IFN as a guidance. When the molecular weight of IFN and the number of primary amino groups are both known, an amount of lactose lactone, which is necessary to modify a desired number of primary amino group, can be determined. Lactose lactone is usually used in an amount of from about 0.5 to 50 mols, preferably from about 10 to 30 mols per mol of the primary amino group of IFN.

Decrease of IFN activity can be prevented by performing the above-mentioned reaction in the presence of a surfactant which does not have an amino group reactive with lactose lactone.

Specific examples of the surfactant include anionic surfactants such as alkylsulfates, e.g., dodecyl sulfates (sodium dodecyl sulfate, lithium dodecyl sulfate and calcium dodecyl sulfate); and nonionic surfactants such as polyoxyethylene ethers such as Triton series surfactants (octoxynol; polyoxyethylene p-t-octylphenyl ethers), e.g., Triton X-100, X-114, X-102 and X-165 and Brij series surfactants (polyoxyethylene alkyl ethers), e.g., Brij 35 and 58, and polyoxyethylene sorbitan alkyl esters such as Tween series surfactants, e.g., Tween 20, 40, 60, 80 and 85. An alkylsulfate such as sodium dodecyl sulfate (SDS) is preferably used.

The concentration of surfactant existed in the reaction mixture is preferably from 0.01 to 1%(w/v), more preferably from 0.1 to 0.3%(w/v).

After completion of the reaction, the reaction product is isolated and purified by means of general procedures for proteins, such as dialysis, salting out, ultrafiltration, ion-exchange chromatography, gel filtration, high performance liquid chromatography, electrophoresis, and so on.

Besides, the above-mentioned surfactant is added to the solvent for dialysis at the same concentration as described above in advance.

Taking advantage of the affinity between galactose and the liver parenchymatous cells, the galactose-modified IFN of the present invention can selectively and efficiently bring IFN to the liver tissue and manifests the effects IFN particularly in the treatment or prevention of hepatic diseases, such as liver cancer, liver cirrhosis, and hepatitis. Sugar-modified IFN of the present invention is particularly effective against hepatitis B or C. In addition, the sugar-modified IFN of the present invention has an extended in vivo half-life and therefore exhibits long-lasting effects.

The sugar-modified IFN of the present invention can be formulated into appropriate preparation forms (e.g., injectable solutions, suppositories, pessaries, inhalants, aerosol, tablets and capsules) together with conventional carriers, diluents, stabilizing agents, excipients and the like, and orally or non-orally administered to mammals inclusive of humans, monkeys, dogs, swines, rabbits, mice and rats. Preferred preparation form is an injectable solution.

Especially, in order to gain full effects on hepatic disease, it is preferable to administer the composition by intravenous injection. Liquid preparations such as injections and the like may be produced by dissolving the sugar-modified IFN in distilled water for injection together, if necessary, with pH-adjusting agents (hydrochloric acid, sodium hydroxide, lactic acid, sodium lactate, disodium hydrogenphosphate, sodium dihydrogenphosphate and the like) isotonizing agents (sodium chloride, potassium chloride, glucose and the like) and stabilizing agents (serum albumin, gelatin, surfactants, glucose, mannose, galactose, maltose, lactose, sucrose, mannitol and the like), subjecting the resulting solution to sterile filtration and then filling the sterile soultion into ampules. Alternatively, to this solution may be further added stabilizing agents or excipients (mannitol, dextrin, cyclodextrin, gelatin and the like) and then the resulting solution is lyophilized in vacuo to serve as preparations for injection which are dissolved upon use. Also, emulsions for injection may be produced by adding an emulsifying agent such as lecithin, Polysorbate 80 (Atlas Co.), polyoxyethylene hydrogenated castror oil or the like to the sugar-modified IFN and emulsifying the mixture in water.

For example, for use as an antiviral or antitumor agent, an injectable solution can be administered once to four times a day at a dose of about $0.1 \times 10^5$ to $100 \times 10^5$, preferably about $0.5 \times 10^5$ to $30 \times 10^5$, more preferably about $1 \times 10^5$ to $10 \times 10^5$ units/day/adult in terms of IFN-α.

Physiological activity of sugar-modified IFN-α was confirmed by intravenously injecting it to a mouse in the following examples. Unmodified IFN-α is widely used for treating human. Since modified IFN-α has the same activity as unmodified IFN-α, sugar-modified IFN-α of the present invention is also effective for treating human, exhibits high accumulating properties in the liver and an extended in vivo half-life. The sugar-modified IFN is effective in lower dose than that of unmodified IFN. Further, other IFNs than IFN-α such as IFN-β also can obtain the same effects as IFN-α by employing the process for modifying IFN-α with sugar of the present invention from the physiological data of the present invention.

The present invention will now be illustrated in greater detail by way of Examples, but it should be understood that the present invention is not to be construed as being limited thereto. All the percents are given by weight.

REFERENCE EXAMPLE

Preparation of Lactose Lactone

1) Preparation of Lactobionate

In 450 ml of water was dissolved 26 g of lactose, and 35 ml of methanol was added thereto. Then, 600 ml of methanol containing 37.45 g of iodine was further added thereto at 40° C., followed by addition of 875 ml of a 4% aqueous solution of potassium hydroxide (potassium hydroxide content: 35.2 g). The mixture was allowed to react at 40° C. for 60 minutes until the color of iodine disappeared, followed by cooling with ice. To the reaction mixture was added 1000 ml of methanol, and the precipitate was collected by filtration, washed with cold methanol and ethyl ether, and dissolved in 150 ml of water. Methanol was again added thereto, and the precipitate was collected by filtration to obtain 18 g of lactobionate, i.e., a compound in which the glucose moiety of lactose is opened and the carboxyl group at the 1-position forms a potassium salt.

2) Preparation of Lactose Lactone

Ten grams of lactanate prepared in (1) above were dissolved in 200 ml of water, and the solution was passed through a column packed with Dowex 50 ($H^+$) to convert the lactanate into a free form, which was concentrated and, after addition of methanol, further concentrated. Methanol was distilled off, and ethanol was added to the residue. The precipitate was collected by filtration to obtain lactose lactone.

EXAMPLE 1

Modification of IFN-α with Lactose Lactone (1)

1) Modification:

A 0.1% aqueous solution of sodium dodecylsulfate (SDS) containing 12.3, 61.5, 184.5 or 307.5 μg of lactose lactone was added to 0.05 ml of an IFN solution (350 MU/ml/1.7 mg-protein; "MU" is abbreviation of "mega units") of human lymphoblast origin (natural type IFN-α; "Sumiferon" produced by Sumitomo Pharmaceuticals Co., Ltd.; molecular weight: 17000 to 30000; 10 lysine residues/molecule), and the system was allowed to react at room temperature for 48 hours. The reaction mixture was dialyzed against water containing 0.1% SDS. The resulting lot was designated LL-IFN-1, 2, 3 or 4, respectively.

2) Physiological Activities

In Table 1 below are shown percent retention of IFN-α activity and IFN-α-induced production of 2'-5'-linked oligoadenylic acid 5'-triphosphate (2-5A) which has an antiviral function.

The activity titer was measured by a dye-exclusion test using an FL cells (cells derived from human amnion tissue)/sindbis virus system and expressed in terms of 50% cytopathic effect ($CPE_{50}$). WHO lymphoblast IFN was used as a standard preparation.

Each test sample (protein content: 0.068 mg) was intravenously injected to an ICR mouse (name of mouse strain). After 24 hours, the liver was minced and centrifuged at 4° C. and 17000×g for 15 minutes, and the 2-5A-producing capability of the supernatant liquor was measured based on the rise in 2-5A synthetase (2-5AS) level. Measurement of 2-5AS activity was made by using a 2-5A Radioimmunoassay Kit sold by Eiken Chemical Co., Ltd. as follows (WO 82/01773). Poly(I): poly(C) agarose gel was added to 50 μl of a sample under assay, and the system was allowed to stand at room temperature for 10 minutes to let the gel adsorb 2-5AS and to activate 2-5AS. After removing assay-obscuring matter by washing with 1 ml of a buffer solution, 500 μl of adenosine 5'-triphosphate (ATP) was added, followed by allowing the mixture to react at 37° C. for 1 hour. To the thus produced 2-5A were added 100 μl each of $^{125}$I-labeled 2-5A solution and an anti-2-5A antiserum suspension to cause competitive reaction at 37° C. for 1 hour. The reaction mixture was centrifuged at 2000×g for 30 minutes, and the supernatant liquor was discarded. The radioactivity of the residual solid was measured. The percent binding of the antibody to the $^{125}$I-labeled 2-5A added was calculated, and the 2-5A produced by 2-5AS in the sample was determined from a previously prepared calibration curve. The results obtained are shown in Table 1.

TABLE 1

| Lot No. | Activity Retention (%) | 2-5A Production (femto mol/mg-protein liver/hr) |
|---|---|---|
| LL-IFN-1 | 82.4 | 54.4 |
| LL-IFN-2 | 82.4 | 31.2 |
| LL-IFN-3 | 74.5 | 39.4 |
| LL-LFN-4 | 55.1 | 67.1 |
| IFN | 100 | 47.4 |
| Control |  | 6.5 |

3) In vivo Behavior

LL-IFN-4 was labeled with [2,3-$^3$H] succinimidyl propionate to prepare $^3$H-LL-IFN-4 of 2670 kBq/mg. $^3$H-IFN of 2007 kBq/mg was also prepared. Each of $^3$H-LL-IFN-4 and $^3$H-IFN in an amount corresponding to 10 μg of protein was injected into the tail vein of 6-week-old male $C_3$H/HeN mice. After the administration, the animals were sacrificed at various times, and the radioactivity of the blood, liver, and kidney was measured to examine in vivo behavior. The results obtained are shown in Table 2 below.

TABLE 2

| Sample | Time After Administration (min) | In vivo Behavior (% ID/g) | | |
|---|---|---|---|---|
| | | Blood | Liver | Kidney |
| $^3$H-IFN | 5 | 12.06 | 4.31 | 99.5 |
| | 15 | 6.08 | 2.61 | 163.9 |
| | 30 | 6.99 | 1.67 | 38.8 |
| | 60 | 5.26 | 1.93 | 21.9 |
| $^3$H-LL-IFN-4 | 5 | 5.61 | 27.5 | 56.2 |
| | 15 | 3.47 | 17.1 | 75.1 |
| | 30 | 2.62 | 9.0 | 23.2 |
| | 60 | 1.84 | 4.8 | 12.6 |

EXAMPLE 2

Modification of IFN-α with Lactose Lactone (2)

1) Modification

A 0.1% SDS aqueous solution containing 3.075 mg of lactose lactone was added to 0.5 ml of IFN-α (350 MU/ml/1.7 mg-protein), and the mixture was allowed to react at room temperature for 96 hours. The reaction mixture was worked up in the same manner as in Example 1 to obtain sugar-modified IFN-α, designated LL-IFN-5.

2) Physiological Activities

The IFN-α activity retention of LL-IFN-5 was 20.7%.

LL-IFN-5 or IFN-α was administered to ICR mice at a dose of 10 MU/57.8 μg-protein. The animals were sacrificed after 3, 6 or 24 hours from administration, and the 2-5A-producing capability in the liver was measured in the same manner as in Example 1. The results obtained are shown in FIG. 1.

FORMULATION EXAMPLE 1

| LL-IFN-4 | 500,000 units |
|---|---|
| Sodium chloride | 8.0 mg |
| Dibasic sodium phosphate | 1.74 mg |
| Monobasic potassium phosphate | 0.2 mg |
| Potassium chloride | 0.2 mg |
| Albumin (human) | 1.0 mg |

The above components are dissolved in sterile distilled water for injection sufficient for forming a solution and the resulting solution is placed in a sterile vial (1 ml) and stored at 2 to 10 degrees centigrade.

FORMULATION EXAMPLE 2

| LL-IFN-5 | 1,000,000 units |
|---|---|
| Sodium chloride | 9.0 mg |
| Albumin (human) | 5.0 mg |

The above components are dissolved in sterile distilled water for injection sufficient to form a solution and the resulting solution is placed in a sterile vial (1 ml) and stored at 2 to 10 degrees centigrade.

The sugar-modified IFN according to the present invention has extremely high accumulating properties in the liver and an extended in vivo half-life as compared with unmodified IFN. Therefore, it achieves extremely high therapeutic or prophylactic effects on hepatic diseases, such as liver cancer (hepatic carcinoma), liver cirrhosis, and hepatitis (e.g., hepatitis B or C) as compared with unmodified IFN.

While the invention has been described in detail and with reference to specific examples thereof, it will be apparent to one skilled in the art that various changes and modifications can be made therein without departing from the spirit and scope thereof.

What is claimed is:

1. Sugar-modified interferon (IFN), which is a binding reaction product between the carbonyl group of a lactose lactone represented by

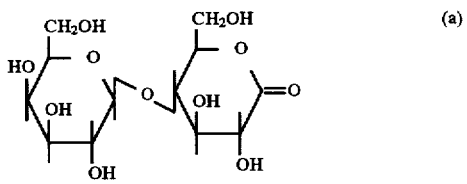 (a)

and an ε-amino group of a lysine residue and/or an amino group at the N-terminal of interferon represented by (b) $R(NH_2)_m$ through acid amido bond to yield (c)

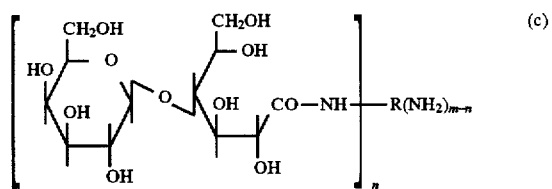 (c)

wherein m is the number of primary amino groups in IFN; n is the number of acid amido bonds; R is the IFN skeleton; and m is greater than or equal to n; and said reaction is performed in the presence of a surfactant which does not have an amino group reactive with lactose lactone.

2. The sugar-modified interferon claimed in claim 1, wherein said interferon is interferon-α or interferon-β.

3. A process for producing sugar-modified interferon which comprises reacting lactose lactone with interferon in an aqueous solvent at a temperature of from 0° to 45° C.

4. The process for producing sugar-modified interferon claimed in claim 3, wherein said reaction is performed in the presence of a surfactant which does not have an amino group reactive with lactose lactone.

5. The process for producing sugar-modified interferon claimed in claim 4, wherein said surfactant is an anionic surfactant or a nonionic surfactant.

6. The process for producing sugar-modified interferon claimed in claim 5, wherein said anion surfactant is alkylsulfate.

7. The process for producing sugar-modified interferon claimed in claim 6, wherein said alkylsulfate is docecyl sulfate.

8. The process for producing sugar-modified interferon claimed in claim 4, wherein dialysis against a surfactant solution is carried out after said reaction.

9. A sugar-modified interferon composition which comprises the sugar-modified interferon claimed in claim 1 and another component selected from the group consisting of carriers, diluents, stabilizing agents, excipients, and mixtures thereof.

10. The sugar-modified interferon composition claimed in claim 9 which is prepared in the form of an injectable solution.

11. A method for treating hepatic diseases treatable with interferon which comprises administering to animals or humans an effective amount of the sugar-modified interferon claimed in claim 1.

12. The method in claim 11, wherein an injectable solution of the sugar-modified interferon is administered once to four times a day at a dose of about $0.1 \times 10^5$ to $100 \times 10^5$ units/day/adult in terms of interferon.

13. The interferon claimed in claim 1, wherein said surfactant is an anionic surfactant or a nonionic surfactant.

14. The interferon claimed in claim 13, wherein said anionic surfactant is alkylsulfate.

15. The interferon claimed in claim 14, wherein said alkylsulfate is dodecyl sulfate.

* * * * *